(12) United States Patent
Kim et al.

(10) Patent No.: US 8,366,619 B2
(45) Date of Patent: Feb. 5, 2013

(54) NODULE SCREENING USING ULTRASOUND ELASTOGRAPHY

(75) Inventors: Yongmin Kim, Lake Forest Park, WA (US); Manjiri Dighe, Bellevue, WA (US); Si Luo, Seattle, WA (US); Jae Kim, Torrance, CA (US); Eung-Hun Kim, Bothell, WA (US)

(73) Assignee: University of Washington, Seattle, WA (US)

( * ) Notice: Subject to any disclaimer, the term of this patent is extended or adjusted under 35 U.S.C. 154(b) by 65 days.

(21) Appl. No.: 12/779,903

(22) Filed: May 13, 2010

(65) Prior Publication Data

US 2010/0292571 A1 Nov. 18, 2010

Related U.S. Application Data

(60) Provisional application No. 61/177,940, filed on May 13, 2009, provisional application No. 61/334,538, filed on May 13, 2010.

(51) Int. Cl.
*A61B 8/00* (2006.01)

(52) U.S. Cl. ........ 600/437; 600/407; 600/438; 600/442; 600/443; 382/128; 382/130; 382/131

(58) Field of Classification Search .................. 600/411, 600/437, 438, 442; 382/128, 130, 131
See application file for complete search history.

(56) References Cited

U.S. PATENT DOCUMENTS

| | | | |
|---|---|---|---|
| 6,277,074 B1 | 8/2001 | Chaturvedi et al. | |
| 7,223,241 B2* | 5/2007 | Radulescu | 600/443 |
| 2004/0015079 A1* | 1/2004 | Berger et al. | 600/437 |
| 2004/0034304 A1 | 2/2004 | Sumi | |
| 2004/0116813 A1 | 6/2004 | Selzer et al. | |
| 2006/0173320 A1* | 8/2006 | Radulescu | 600/438 |
| 2007/0055448 A1* | 3/2007 | Mendrick et al. | 702/19 |
| 2007/0093716 A1* | 4/2007 | Radulescu | 600/437 |
| 2008/0285819 A1* | 11/2008 | Konofagou et al. | 382/128 |
| 2010/0063393 A1* | 3/2010 | Moradi et al. | 600/442 |
| 2010/0094131 A1 | 4/2010 | Bae et al. | |
| 2010/0121178 A1* | 5/2010 | Krishnan et al. | 600/411 |
| 2011/0130660 A1* | 6/2011 | Cloutier et al. | 600/438 |

FOREIGN PATENT DOCUMENTS

WO 2006/026552 A1 3/2006

OTHER PUBLICATIONS

Bae, U., and Y. Kim, "Angular Strain Estimation Method for Elastography," IEEE Transactions on Ultrasonics, Ferroelectrics, and Frequency Control 54(12):2653-2661, Dec. 2007.

Bae, U., et al., "Thyroid Elastography Using Carotid Artery Pulsation: A Feasibility Study," IEEE Ultrasonics Symposium, Vancouver, Canada, Oct. 2-6, 2006, pp. 614-617.

Bae, U., et al., "Ultrasound Thyroid Elastography Using Carotid Artery Pulsation: Preliminary Study," Journal of Ultrasound in Medicine 26(6):797-805, Jun. 2007.

Capelli, C., et al., "Fine Needle Cytology of Complex Thyroid Nodules," European Journal of Endocrinology 157(4):529-532, Oct. 2007.

(Continued)

*Primary Examiner* — Tse Chen
*Assistant Examiner* — Baisakhi Roy
(74) *Attorney, Agent, or Firm* — Dorsey & Whitney LLP (57) ABSTRACT

A medical device is configured to diagnose whether a nodule of a bodily organ is malignant or benign using ultrasound elastography to determine a nodule stiffness index. Using either an external compression source or an in vivo pulsation source, the stiffness of the nodule of the bodily organ can be quantified by either its static properties or dynamic properties. The nodule can be classified as Type I, which is benign requiring further observation, or Type II, which is malignant requiring invasive procedures.

15 Claims, 7 Drawing Sheets

OTHER PUBLICATIONS

Chow, S.-M., et al., "Papillary Microcarcinoma of the Thyroid—Prognostic Significance of Lymph Node Metastasis and Multifocality," Cancer 98(1):31-40, Jul. 2003.

Cinthio, M., et al., "Longitudinal Movements and Resulting Shear Strain of the Arterial Wall," American Journal of Physiology: Heart and Circulatory Physiology 291(1):H394-H402, Jul. 2006.

Cooper, D.S., et al., "Management Guidelines for Patients With Thyroid Nodules and Differentiated Thyroid Cancer," Thyroid 16(2):1-33, Feb. 2006.

Dighe, M., et al., "Differential Diagnosis of Thyroid Nodules With US Elastography Using Carotid Artery Pulsation," Radiology 248(2):662-669, Aug. 2008.

Frates, M.C., et al., "Management of Thyroid Nodules Detected at US: Society of Radiologists in Ultrasound Consensus Conference Statement," Radiology 237(3):794-800, Dec. 2005.

Frates, M.C., et al., Prevalence and Distribution of Carcinoma in Patients With Solitary and Multiple Thyroid Nodules on Sonography 91(9):3411-3417, Sep. 2006.

Gao, L., et al., "Imaging of the Elastic Properties of Tissue—A Review," Ultrasound in Medicine and Biology 22(8):959-977, 1996.

Garra, B.S., et al., "Elastography of Breast Lesions: Initial Clinical Results," Radiology 202(1):79-86, Jan. 1997.

Gharib, H., "Chapter 6d. Fine-Needle Aspiration Biopsy of the Thyroid Gland," Thyroid Disease Manager, Feb. 1, 2008, <http://www.thyroidmanager.org/Chapter6a/chapter6d.pdf>.

Gharib, H., and J.R. Goellner, "Fine-Needle Aspiration Biopsy of the Thyroid: An Appraisal," Annals of Internal Medicine 118(4):282-289, Feb. 1993.

Gharib, H., et al., "American Association of Clinical Endocrinologists, Associazione Medici Endocrinologi, and European Thyroid Association Medical Guidelines for Clinical Practice for the Diagnosis and Management of Thyroid Nodules," Endocrine Practice 16(Suppl 1):1-43, May/Jun. 2010.

Greenleaf, J.F., et al., "Selected Methods for Imaging Elastic Properties of Biological Tissues," Annual Review of Biomedical Engineering 5:57-78, Aug. 2003.

Hay, I.D., et al., "Papillary Thyroid Microcarcinoma: A Study of 900 Cases Observed in a 60-Year Period," Surgery 144(6):980-988, Dec. 2008.

Hegedüs, L., "Clinical Practice. The Thyroid Nodule," New England Journal of Medicine 351(17):1764-1771, Oct. 2004.

Hegedüs, L., et al., "Management of Simple Nodular Goiter: Current Status and Future Perspectives," Endocrine Reviews 24(1):102-132, Feb. 2003.

Lyshchik, A., et al., "Elastic Moduli of Thyroid Tissues Under Compression," Ultrasonic Imaging 27(2):101-110, Apr. 2005.

Lyshchik, A., et al., "Thyroid Gland Tumor Diagnosis at US Elastography," Radiology 237(1):202-211, Oct. 2005.

Mazzaferri, E.L., and S.M. Jhiang, "Long-Term Impact of Initial Surgical and Medical Therapy on Papillary and Follicular Thyroid Cancer," American Journal of Medicine 97(5):418-428, Nov. 1994.

McCartney, C.R., and G.J. Stukenborg, "Decision Analysis of Discordant Thyroid Nodule Biopsy Guideline Criteria," Journal of Clinical Endocrinology and Metabolism 93(8), Aug. 2008, 19 pages.

Moon, W.-J., et al., "Benign and Malignant Thyroid Nodules: US Differentiation—Multicenter Retrospective Study," Radiology 247(3):762-770, Jun. 2008.

Moon, W.K., et al., "Analysis of Elastographic and B-Mode Features at Sonoelastography for Breast Tumor Classification," Ultrasound in Medicine and Biology 35(11):1794-1802, Nov. 2009.

Ophir, J., et al., "Elastography: A Quantitative Method for Imaging the Elasticity of Biological Tissues," Ultrasonic Imaging 13(2):111-134, Apr. 1991.

Ophir, J., et al., "Elastography: Ultrasonic Estimation and Imaging of the Elastic Properties of Tissues," Proceedings of the Institution of Mechanical Engineers. Part H: Journal of Engineering in Medicine 213(3):203-233, 1999.

Ortiz, R., et al., "Effect of Early Referral to an Endocrinologist on Efficiency and Cost of Evaluation and Development of Treatment Plan in Patients With Thyroid Nodules," Journal of Clinical Endocrinology and Metabolism 83(11):3803-3807, Nov. 1998.

Raab, S.S., et al., "Effectiveness of Toyota Process Redesign in Reducing Thyroid Gland Fine-Needle Aspiration Error," American Journal of Clinical Pathology 126(4):585-592, Oct. 2006.

Rago, T., et al., "Elastography: New Developments in Ultrasound for Predicting Malignancy in Thyroid Nodules," Journal of Clinical Endocrinology & Metabolism 92(8):2917-2922, Aug. 2007.

Tan, G.H., and H. Gharib, "Thyroid Incidentalomas: Management Approaches to Nonpalpable Nodules Discovered Incidentally on Thyroid Imaging," Annals of Internal Medicine 126(3):226-231, Feb. 1997.

Tranquart, F., et al., "Elastosonography of Thyroid Lesions," Journal of Radiology 89(1 Pt 1):35-39, Jan. 2008.

Wartofsky, L., "Thyroid Cancer: A Comprehensive Guide to Clinical Management," Humana Press, Totowa, New Jersey, 2000, reviewed by J.E. Freitas in Journal of Nuclear Medicine 42(6):984-985, Jun. 2001.

Yeung, M.J., and J.W. Serpell, "Management of the Solitary Thyroid Nodule," Oncologist 13(2):105-112, Feb. 2008.

Wilson, et al., "Ultrasonic Measurement of Small Displacements and Deformations of Tissue", Ultrasonic Imaging vol. 4 Iss. 1, 1982, 71-82.

* cited by examiner

NODULE SCREENING USING ULTRASOUND ELASTOGRAPHY

CROSS-REFERENCES TO RELATED APPLICATIONS

The application claims the benefit of U.S. provisional application No. 61/177,940, filed May 13, 2009; and U.S. provisional application No. 61/334,538, filed May 13, 2010, the disclosures of which are hereby expressly incorporated by reference in their entirety.

BACKGROUND

The diagnosis for a thyroid nodule's malignancy is currently made via fine needle aspiration (FNA) biopsy. It is estimated that around 300,000 thyroid FNA biopsies are performed in the United States annually. However, about seventy percent of these biopsies turn out to be benign. As biopsies are an invasive procedure, a better diagnostic method executed by a medical device is desired to reduce the number of biopsies being performed on benign nodules.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

One aspect of the subject matter includes a device form. The device form is recited to include a medical device for diagnosing malignant nodules in a bodily organ, which comprises an ultrasound elastographer configured to produce elastography information generated by either in vivo compression or external compression of the bodily organ. The medical device further comprises a benign/malignant scorer configured to transform elastography information of each nodule into a nodule stiffness index. The medical device yet further comprises a nodule screener configured to classify a nodule as Type I, which is benign for further observation, or as Type II, which is malignant for invasive procedures.

Another aspect of the subject matter includes a method form. The method form is recited to include a method for diagnosing benign nodules in a bodily organ, which comprises performing an elastography process to derive quantitative information on tissue stiffness so as to produce a set of strain frames. The method further comprises calculating for each nodule a nodule stiffness index using the set of strain frames. The method yet further comprises screening each nodule to classify the nodule as Type I, which is benign for further observation, or as Type II, which is malignant for invasive procedures.

Another aspect of the subject matter includes a computer-readable medium form. The computer-readable medium form is recited to include a computer-readable medium having computer-executable instructions stored thereon for implementing a method for diagnosing benign nodules in a bodily organ, which comprises performing an elastography process to derive quantitative information on tissue stiffness so as to produce a set of strain frames. The computer-readable medium further comprises calculating for each nodule a nodule stiffness index using the set of strain frames. The computer-readable medium yet further comprises screening each nodule to classify the nodule as Type I, which is benign for further observation, or as Type II, which is malignant for invasive procedures.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
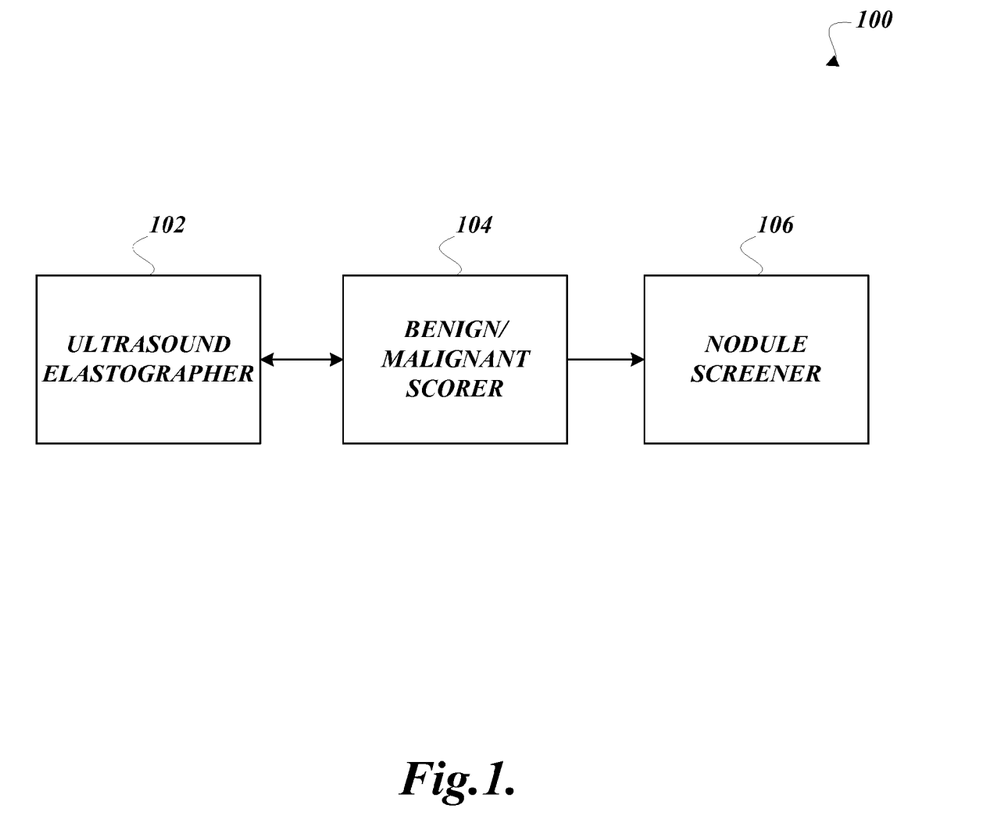
FIG. 1 is a pictorial diagram illustrating an archetypical medical device configured to diagnose whether a nodule is benign or malignant.

A medical device 100 to assist in diagnosing nodule malignancy is illustrated by FIG. 1. In one embodiment of the present subject matter, the medical device 100 includes an ultrasound elastographer 102. In other embodiments of the present subject matter, the medical device 100 lacks the ultrasound elastographer 102, and in these embodiments, the medical device 100 receives nodule information from third-party ultrasound machinery. The ultrasound elastographer 102, in all embodiments, functions to quantify ultrasound information so as to transform into nodule information, such as tissue strain. In all embodiments, the medical device 100 includes a benign/malignant scorer 104 which scores various nodules by transforming pieces of nodule information into a nodule stiffness index, which is quantitative not qualitative. In various embodiments, the nodule stiffness index can be calculated from any suitable methods. Some suitable methods include ratios of static properties, variants of dynamic properties, decisions by an artificial neural network, results from support vector machines, Bayesian network, Adaboost, decision tree, random forest, or discriminant scores produced by a linear discriminant analysis.

In all embodiments, the medical device 100 includes a nodule screener 106 for screening nodules as Type I, probably benign requiring observation over time, or Type II, probably malignant requiring invasive medical procedures. To classify a nodule as Type I or Type II, the nodule screener 106 uses classifier parameters based on sensitivity/specificity input received from a user of the medical device 100 or otherwise defaults to classifier parameters that achieve the highest accuracy or reduces false negatives where a malignant nodule is misclassified as benign. The classifier parameters, in one embodiment, may include a constant, but in other embodiments, may include a vector of multiple constants, and in yet other embodiments, may include a multiple dimensional surface. In some embodiments, classifier parameters are not used, and the input into these embodiments is the nodule stiffness index and the output is whether the nodule is of Type I or Type II or other types. The screener 106 may be coupled to a printer or a display or a computer network to output classifying information regarding a particular nodule so that health care providers can use such information in providing care for patients.

The ultrasound elastographer 102 quantifies, using suitable metrics, the stiffness of nodules, such as a thyroid nodule, from a set of strain images (one or more) generated by ultrasound machinery. The stiffness of nodules ultimately helps to classify the nodules into different types, leading to different diagnoses, which facilitate better medical care for patients. Each metric can be computed semiautomatically or automatically to reduce dependency on a user's facility of ultrasound machinery. Although in a few embodiments of the present subject matter the metric is based on external compression sources to test the stiffness of nodules, in the remaining embodiments of the present subject matter the metric is based on suitable in vivo compression sources, such as the carotid artery. The ultrasound elastographer 102, the benign/malignant scorer 104, and the nodule screener 106 may be assembled using hardware, software, or a combination of hardware and software.

FIGS. 2A-2F illustrate a method 2000, executed on the medical device 100, for diagnosing nodules' malignancy using ultrasound elastography. From a start block, the method 2000 proceeds to a set of method steps 2002, defined between a continuation terminal ("Terminal A") and an exit terminal ("Terminal B"). The set of method steps 2002 describes performing ultrasound elastography. See FIG. 2A. From Terminal A (FIG. 2B), the method 2000 proceeds to block 2008 where prior to any invasive procedures, such as fine needle aspiration, ultrasound elastography is performed over a bodily organ of interest, such as a thyroid.

Figure 2A:
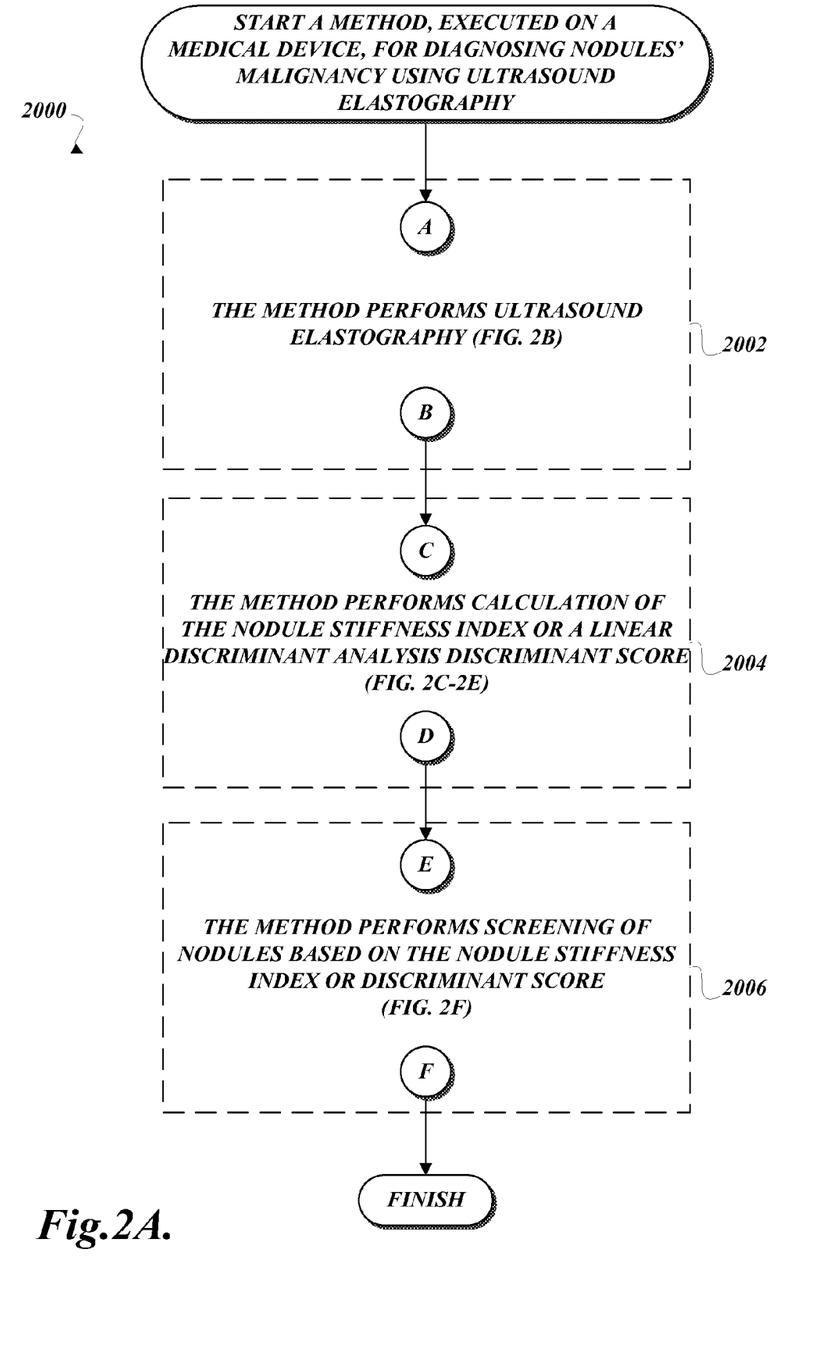
FIGS. 2A-2F are process diagrams illustrating an archetypical method, executed on a medical device, for diagnosing nodules' malignancy using ultrasound elastography.
Figure 2B:
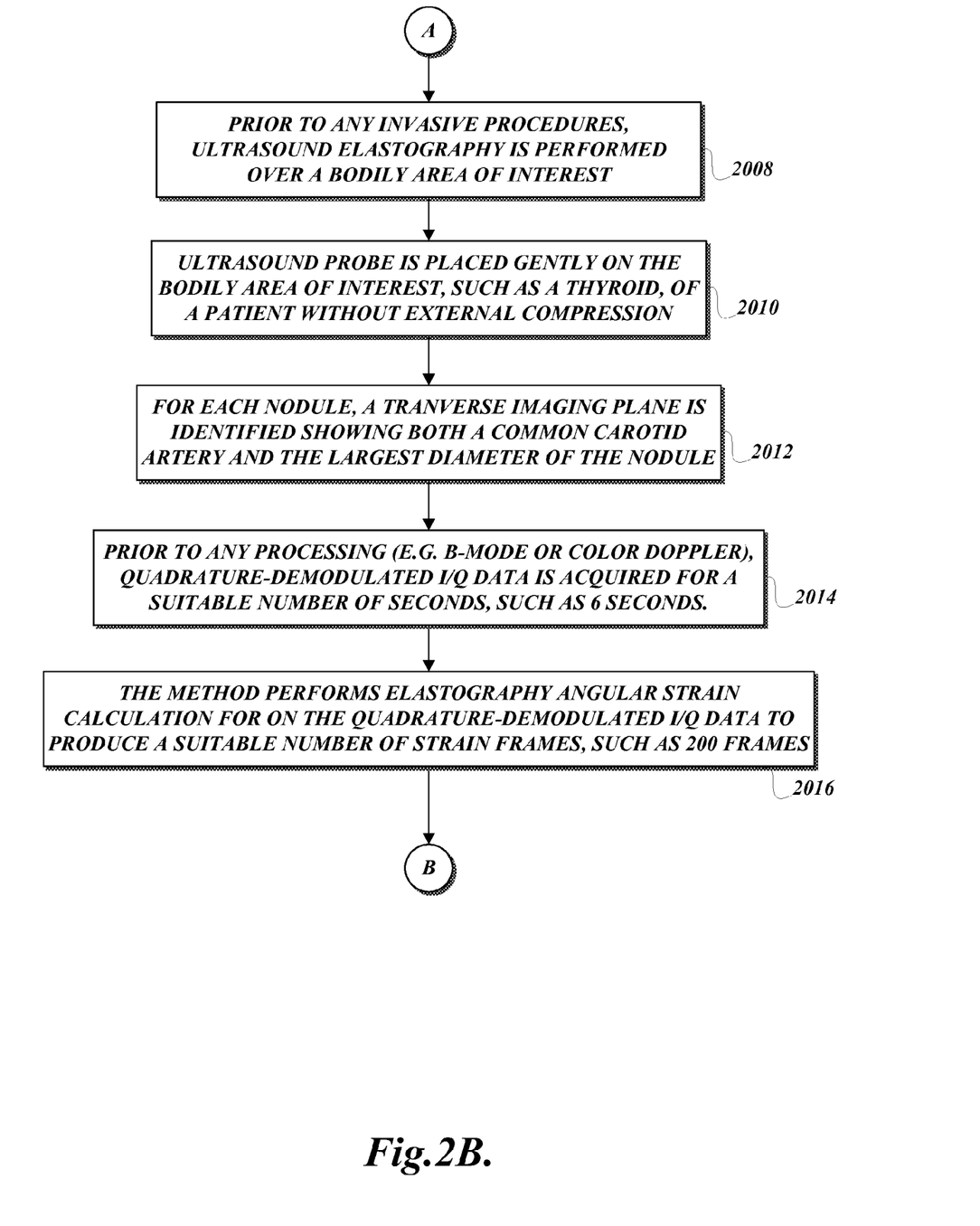

An ultrasound probe from suitable ultrasound machinery, such as a HI VISION 5500 with a 7.5-MHz linear array transducer from Hitachi Medical Systems America in Twinsburg, Ohio, is placed gently on the bodily area of interest. If relying on in vivo compression sources, such as the carotid artery, a transverse plane is searched using the B-Mode of the ultrasound machinery to show the carotid artery and the largest diameter of a nodule. See block 2010 where it is specified that the ultrasound probe is placed gently on the bodily organ of interest, such as the thyroid, of a patient without external compression.

Also at block 2012, for each nodule, the method 2000 identifies a transverse imaging plane showing both the carotid artery and the largest diameter of the nodule. At block 2014, prior to any processing (e.g. B-mode or color Doppler), quadrature-demodulated I/Q data (or other types of data such as pre-beamformed radio frequency (RF) channel data, beamformed RF data, and envelope-detected B-mode data) is acquired for a suitable number of seconds, such as six seconds. The ultrasound elastographer 102 performs an elastography angular strain method on the data to produce a suitable number of strain frames, such as 200 frames. See block 2016. The method then continues to exit Terminal B.

From Terminal B (FIG. 2A), the method 2000 continues to a set of method steps 2004, defined between a continuation terminal ("Terminal C") and an exit terminal ("Terminal D"). The set of method steps 2004 describes performing a calculation of the nodule stiffness index or a linear discriminant analysis score (discriminant score). See FIG. 2A. From Terminal C (FIG. 2C), the method 2000 proceeds to decision block 2018 where a test is performed by the benign/malignant scorer 104 to determine whether the nodule stiffness index is calculated using systolic pressure. If the answer is NO, the method proceeds to another continuation terminal ("Terminal C1").

Figure 2C:
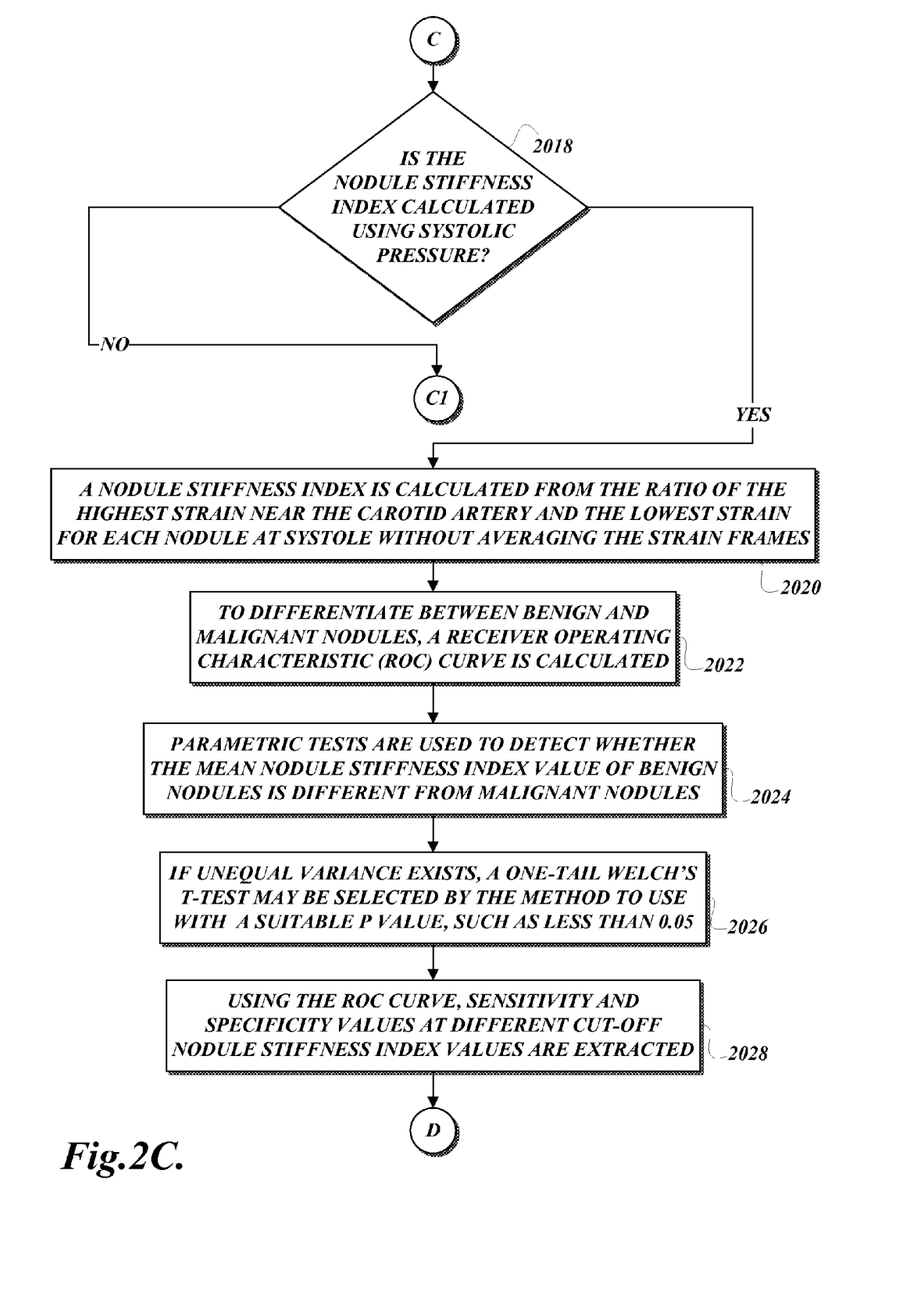

If the answer is YES, the method proceeds to block 2020, where a nodule stiffness index is calculated from the ratio of the highest strain near the carotid artery and the lowest strain for each nodule at systole without averaging the strain frames. For a bodily organ that is near the carotid artery, maximum deformation (strain) occurs during systole when the carotid artery lumen diameter increases to its maximum size due to high systolic pressure. To obtain the ratio, the benign/malignant scorer 104 may analyze a strain frame generated by the angular strain method during systole. The benign/malignant scorer 104 reviews two regions of interest, one being proximal to the carotid artery (location of the highest strain) and the other within the nodule (location of the lowest strain).

The regions of interest may be selected by the benign/malignant scorer 104 in a number of suitable techniques. One suitable technique includes using the B-Mode of the ultrasound machinery to delineate the boundary of the nodule and the area proximal to the carotid artery. Another suitable technique includes using strain distribution information within the nodule to select a region of interest. For each region of interest, a strain value may be generated by averaging all the strain values within a suitable boundary area, such as an area about the size of 2 mm by 2 mm. The benign/malignant scorer 104 repeats this for multiple strain images to derive the nodule stiffness index by dividing the strain value near the carotid artery at systole by a corresponding strain value in the nodule.

The following discussion helps to provide context for how the method 2000 selects either predetermined classifier parameters or receives the desired sensitivity/specificity by the user of the medical device 100 to derive suitable classifier parameters if they are used to differentiate benign nodules from nodules that are malignant. See block 2022. The following steps occur prior to the execution of the method 2000. To help differentiate between benign and malignant nodules, a receiver operating characteristics (ROC) curve is calculated based on previously acquired data and FNA/surgery outcomes. Next, parametric tests are used to detect whether the mean nodule stiffness index value of benign nodules is different from malignant nodules. If unequal variance exists, a one-tailed Welch's t-test may be selected by the method to use with a suitable p-value, such as less than 0.05. Finally, using the ROC curve, sensitivity and specificity values at different nodule stiffness index values are extracted to derive classifier parameters.

From Terminal C1 (FIG. 2D), the method 2000 proceeds to decision block 2030 where a test is performed by the benign/malignant scorer 104 to determine whether the nodule stiffness index is calculated during diastole. If the answer is NO, the method proceeds to another continuation terminal ("Terminal C2"). If the answer is YES, the method proceeds to block 2032, where a nodule stiffness index is calculated by the benign/malignant scorer 104 from the standard deviation of strain in diastole of the carotid artery. The standard deviation of strain in diastole is dependent on the strain variation of a nodule using its dynamic properties in response to an in vivo oscillation source, such as the carotid artery pulsation due to the rhythm of a patient's heart beat. The magnitude of the nodule tissue vibration at the heart beat frequency is inversely proportional to its stiffness. Since a malignant nodule is much stiffer (e.g., three times as much and so on) than a benign nodule, the magnitude of variation for a malignant nodule should be much less (e.g., three times as less and so on) than a benign module. Similarly, it can be inferred that a malignant nodule's natural frequency is higher than that of a benign nodule. This property recognized by the benign/malignant scorer 104 of the medical device 100 can be used to characterize nodules whether they are benign or malignant.

Figure 2D:
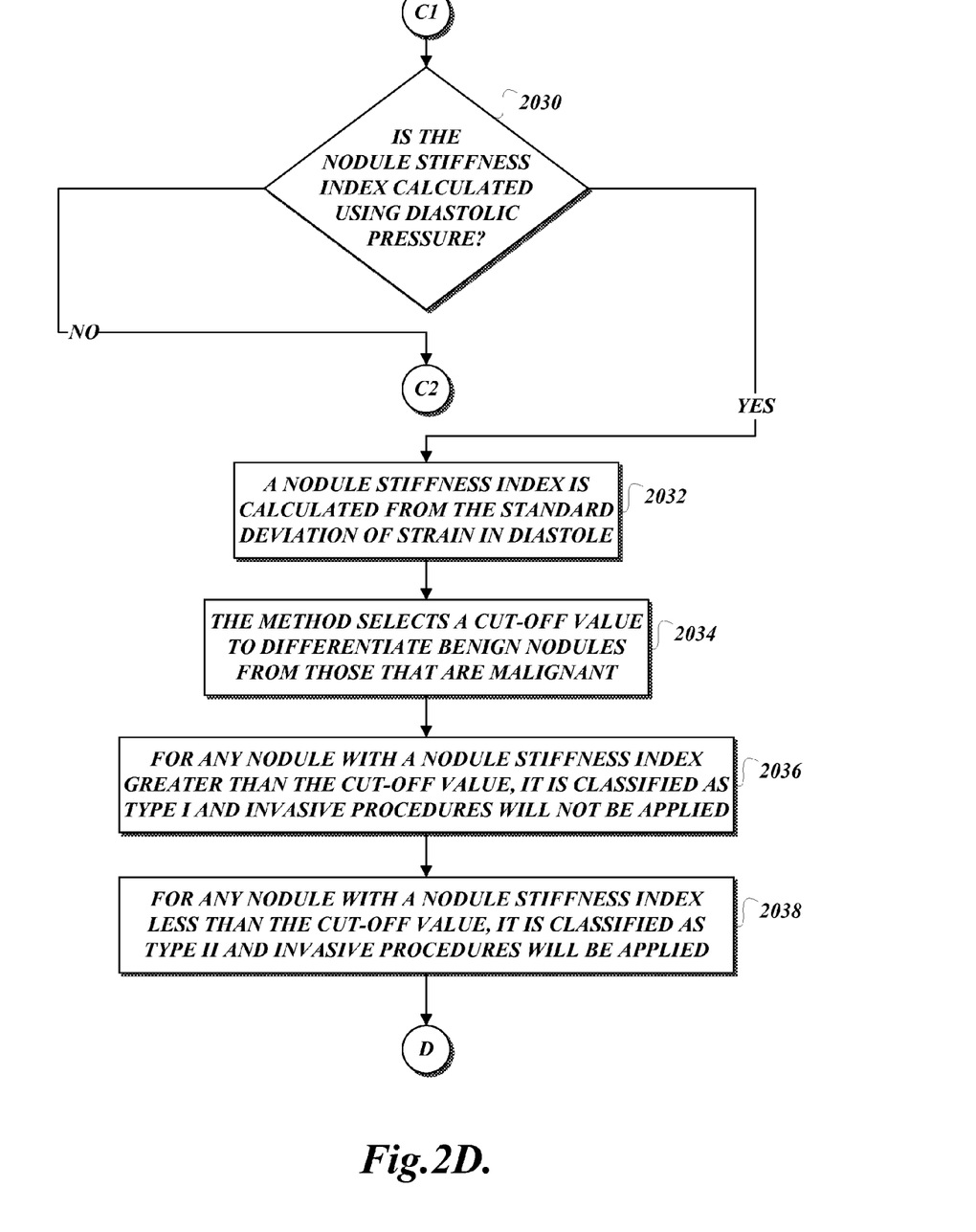

At block 2034, if classifier parameters are used, the method 200 selects predetermined classifier parameters to differentiate benign nodules from those that are malignant unless the user of the medical device 100 has earlier specified classifier parameters in accordance with desired sensitivity/specificity. In some embodiments, the user cannot specify because classifier parameters are preset depending on target bodily organs, transducer types and other ultrasound scanning parameters. Any nodule with a nodule stiffness index greater than the classifier parameters is classified as Type I and invasive procedures are unlikely to be applied as the nodule will be under observation over time. See block 2036. At block 2038, any nodule with a nodule stiffness index less than the classifier parameters is classified as Type II and invasive procedures is likely to be applied.

From Terminal C2 (FIG. 2E), the method 2000 proceeds to decision block 2040 where a test is performed by the benign/malignant scorer 104 to determine whether the nodule stiffness index is calculated using a linear discriminant analysis discriminant score. If the answer is NO, the method may use other suitable techniques to classify nodules in addition to the techniques discussed hereinbefore, and if there are no other suitable techniques, the method 2000 proceeds to another continuation terminal ("Terminal F") and terminates execution.

Figure 2E:
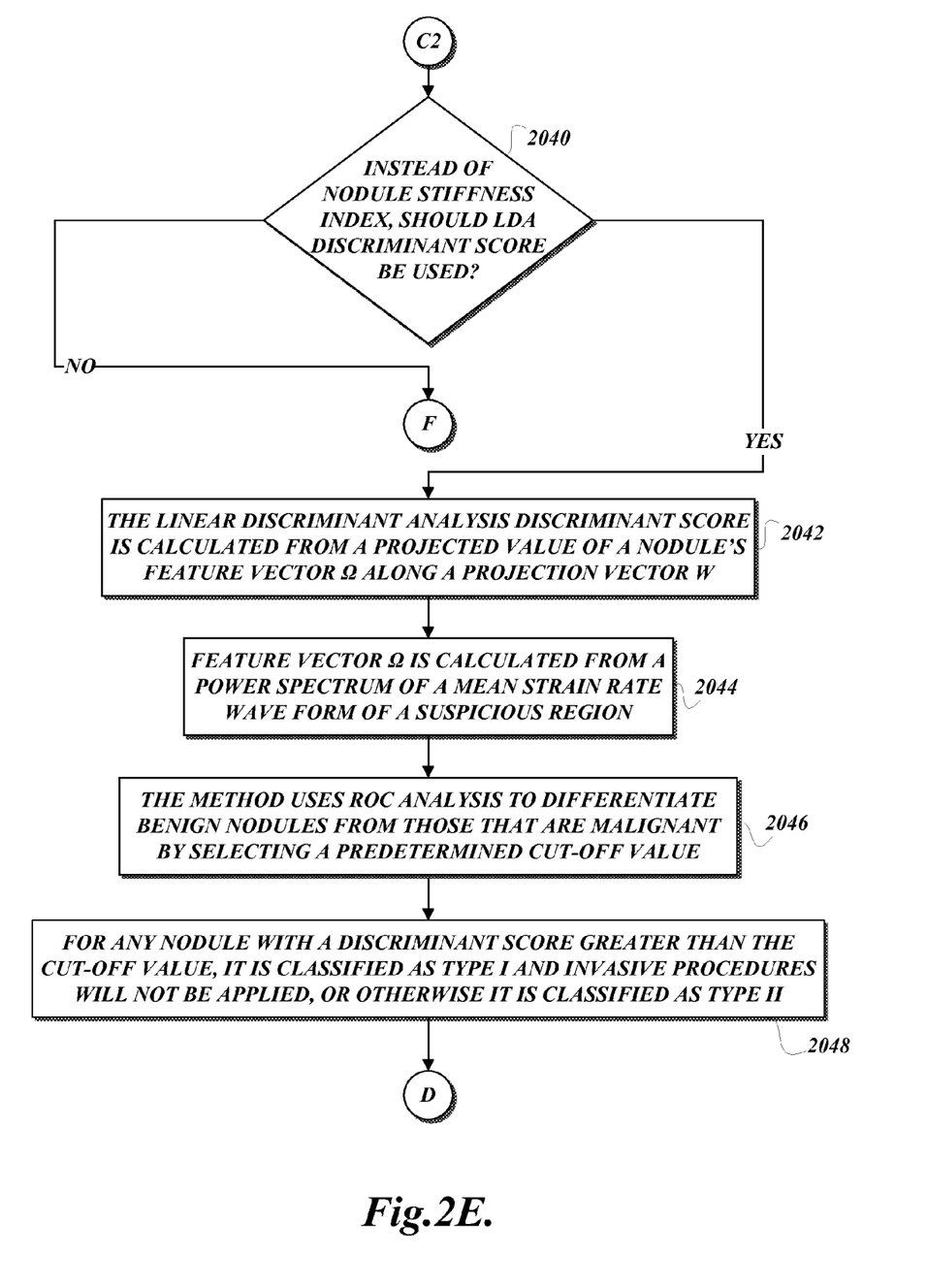

In preparation for calculating the discriminant score, the benign/malignant scorer 104 derives the strain from an angular strain method. A window is then placed within an image that captures a bodily organ of interest, such as the thyroid gland, and its strain is computed by averaging all the strain values in the neighborhood of 2 mm×2 mm. By repeating this over multiple strain images, a strain versus time waveform can be produced. By dividing the time interval between two consecutive frames, the strain rate waveform is generated. The bodily organ expansion in the axial direction during systole results in positive peaks. The strain rate waveform reveals the dynamic deformation of organ tissue in response to the compression from the carotid artery pulsation.

The mechanical property of thyroid tissue can be modeled as a system with a viscous damper and an elastic spring connected in parallel. The pulsation from the carotid artery results in periodic deformation that can be observed in the thyroid tissue. Because of the periodic nature of the input and output, the benign/malignant scorer 104 can analyze the thyroid mechanical model in the frequency domain. The carotid artery pulsation F (f) causes the thyroid tissue deformation X (f) via $$X(f)=H(f)F(f)$$

where H (f) represents the frequency response of thyroid tissue. Due to the difference in H (f), the amount of deformation X (f) for benign and malignant nodules is expected to be different.

For the generated strain rate waveforms, the peaks caused by the systolic blood pressure in the carotid artery lumen at the heart beat frequency (~1 Hz) are observable. Because of the increased stiffness in a malignant nodule, its peak strain magnitude is likely smaller than that of a benign nodule. Another difference between benign and malignant nodules is the oscillation in the strain rate waveform. The strain rate waveform of the benign nodule is likely to show noticeable oscillation, especially during the diastolic period, while the variation in the strain rate of the malignant nodule is minimized. The oscillation frequencies are higher than the heart beat frequency as can be observed in the corresponding power spectrum.

According to an elastic spring model, the oscillation frequency is correlated to the natural frequency of thyroid tissue ($f_n$) by $$f_n = \frac{1}{2\pi}\sqrt{\frac{k}{m}}$$

where m is the mass and k is the spring constant that is proportional to the thyroid tissue stiffness. Differences in the power spectrum are mainly caused by different stiffness in benign and malignant nodules. To analyze the frequency-dependent thyroid tissue deformation at different input frequencies, the carotid artery pulsation is modeled by the benign/malignant scorer 104 as follows:

$$F(t) = \sum_{f=f_h}^{\infty} C_f \cos(2\pi f t)$$

where $f_h$ is the heart beat frequency (~1 Hz) and $C_f$ is the magnitude of compression at a specific frequency f. Since the carotid artery is a low-frequency compression source, the model assumes that the maximum magnitude $C_{max}$ occurs at the heart beat frequency $f_h$ and the magnitude decreases as the frequency increases. Then, the magnitude of thyroid tissue deformation can be calculated as follows:

$$X(f) = \frac{C_f}{k} \frac{1}{\sqrt{(1-r^2)^2 + (2\zeta r)^2}}$$

where $\zeta$ is the damping ratio and r is defined as $$r = \frac{f}{f_n}.$$

In the above equation, various frequency components from the carotid artery pulsation would deform the tissue at their respective frequency, and the magnitude of deformation at a specific frequency is proportional to the ratio of the magnitude of input compression ($C_f$) and tissue stiffness (k). When $$f = f_h, r = \frac{f_h}{f_n} \ll 1.$$

Thus, the above equation can be simplified as follows:

$$X(f_h) \approx \frac{C_{max}}{k}$$

According to the above equation, the magnitude of thyroid tissue deformation at the heart beat frequency is inversely proportional to its spring constant or stiffness. When the input frequency approaches the natural frequency of thyroid tissue, r approaches 1. The magnitude of deformation at $f_n$ can be approximated as $$X(f_n) \approx \frac{C_{f_n}}{\sqrt{k}} \frac{\sqrt{m}}{v}$$

by substituting $$\zeta = \frac{v}{2\sqrt{km}} \text{ into } X(f) = \frac{C_f}{k} \frac{1}{\sqrt{(1-r^2)^2 + (2\zeta r)^2}},$$

where v is the viscosity of a nodule. Assuming that the mass (m) and viscosity (v) for benign and malignant nodules are similar, the above equation can be simplified as follows:

$$X(f_n) \propto \frac{C_{f_n}}{\sqrt{k}}$$

which suggests that $X(f_n)$ is dependent on both the stiffness of tissue (k) and $C_{f_n}$, which is the compression magnitude at the natural frequency. Due to the high stiffness of a malignant nodule, its natural frequency is higher than that of a benign nodule based on $$f_n = \frac{1}{2\pi}\sqrt{\frac{k}{m}}.$$

Since $C_f$ decreases as the frequency increases, the input component at the natural frequency to deform a malignant nodule is smaller than that of a benign nodule, which leads to smaller $X(f_n)$.

Because of the increased stiffness in malignant nodules, the benign/malignant scorer 104 can observe different frequency-domain characteristics in tissue deformation from those of benign nodules. The benign/malignant scorer 104 can utilize this difference in performing the thyroid nodule classification. Although the above technique may suitably be used for any bodily organs that can be modeled by their mechanical representations, for the sake of illustration, the thyroid gland is used as an exemplary bodily organ, and other suitable bodily organs may be used.

The benign/malignant scorer 104 estimates tissue stiffness by deriving the strain rate waveform and evaluating its frequency characteristics. Since a strain rate waveform represents the tissue deformation at a specific location, there are thousands of waveforms to be analyzed depending on the nodule size and parameters used in ultrasound scanning The first step in the classification algorithm is to cluster together the waveforms with similar response to the carotid artery pulsation. A suitable clustering technique, such as k-means clustering, to perform this preprocessing includes the following steps: 1) the boundary of a thyroid nodule is first delineated in the ultrasound B-mode image, and the segmented nodule is considered as a region of interest (ROI); 2) the strain rate waveforms from the ROI are organized into an n (rows) by p (columns) matrix, where n is the number of pixels or measurements within the ROI and p is the number of frames in the elastography data; 3) k rows are randomly selected from the matrix as the mean of each cluster, and k clusters are created by associating each measurement with the nearest mean based on the squared Euclidean distance; 4) the new mean of each of the k clusters is calculated; and 5) steps 3 and 4 are repeated until convergence is reached.

After clustering, the benign/malignant scorer 104 represents the strain rate waveforms averaged over various regions. The benign/malignant scorer 104 detects the mean strain for a region that is lower than the other regions, which indicates that the particular region is stiffer and therefore more suspicious for malignancy determination. Next, the benign/malignant scorer 104 calculates the power spectrum of the mean strain rate waveform corresponding to the detected suspicious region. The power spectrum values at different frequencies, ranging from 0 Hz to a half of the frame rate, are used as features in classification. If it were to denote a feature set as ⌈ with N elements, then a thyroid nodule can be considered as a point ⌈ in the N-dimensional feature space. For example, the power spectrum of a thyroid nodule with 128 bins can be considered as a vector of 128 dimensions or equivalently a point in a 128-dimensional space.

Instead of performing classification directly in a high-dimensional space, the benign/malignant scorer 104 reduces feature dimensionality by converting into a space with fewer dimensions where the classification can be performed more efficiently. Many suitable conversion techniques may be used including principal component analysis. By performing feature dimensionality reduction using principal component analysis, the original N-dimensional feature vector ⌈ is transformed to a new feature vector Ω with M (M<N) dimensions. This feature vector Ω with M dimensions is used for nodule classification via linear discriminant analysis.

Returning to decision block 2040, if the answer is YES, the method proceeds to block 2042, where the linear discriminant analysis discriminant score is calculated by the benign/malignant scorer 104 from a projected value of a nodule's feature vector S2 along a projection vector w. The feature vector S2 is calculated from a power spectrum of a mean strain rate waveform of a suspicious region. See block 2044. At block 2046, the method selects predetermined classifier parameters if they are used by the medical device 100 to differentiate benign nodules from those that are malignant. Any nodule with a discriminant score greater than the classifier parameters is classified as Type I and invasive procedures will not yet be applied in lieu of observation. Otherwise, the nodule is classified as Type II where invasive procedures are likely to be applied. See block 2048.

Figure 2F:
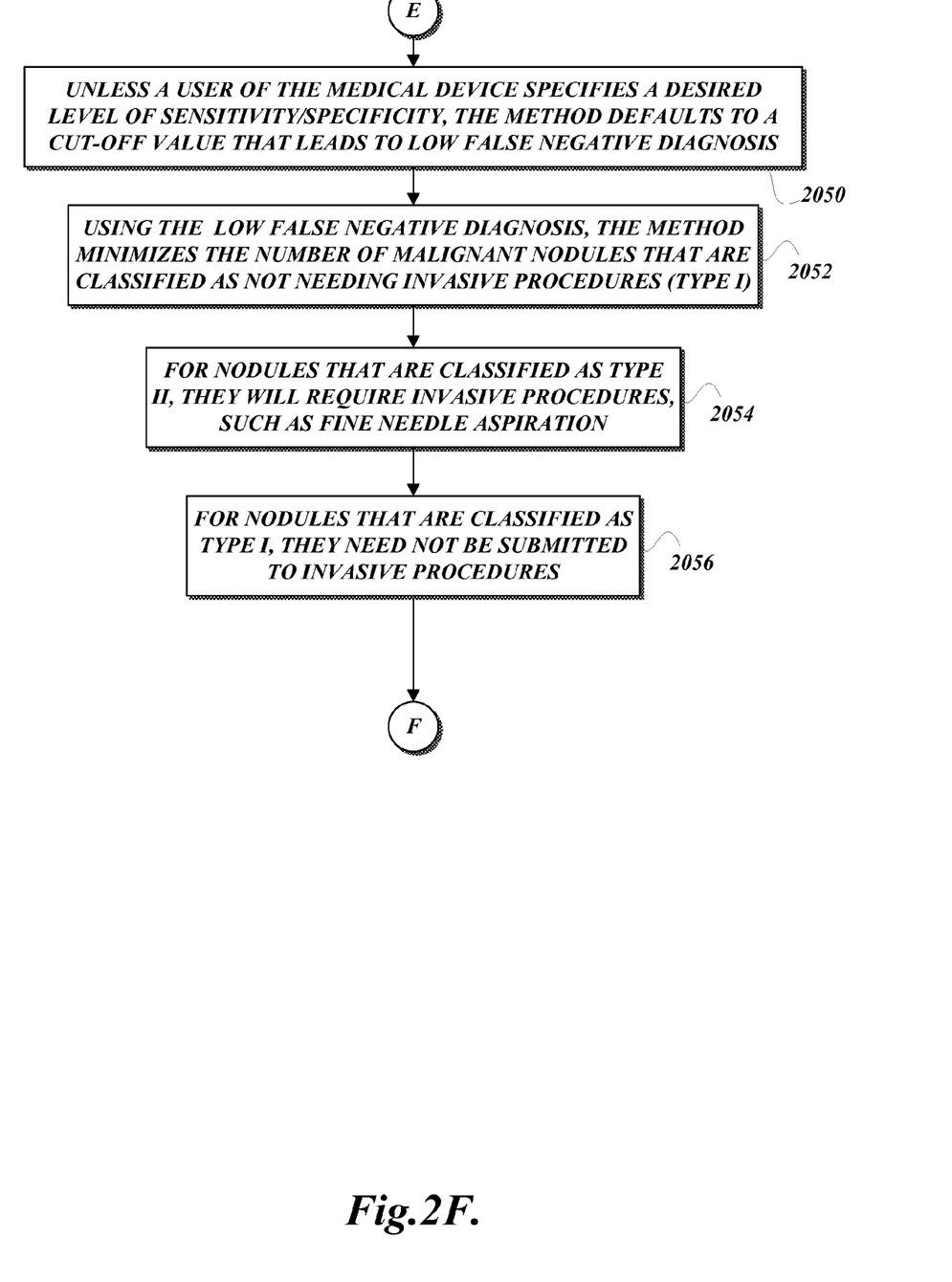

From exit Terminal D, the method 2000 proceeds to a set of method steps 2006, defined between a continuation terminal ("Terminal E") and an exit terminal ("Terminal F"). The set of method steps 2006 describes the screening of nodules by the nodule screener 106 based on the nodule stiffness index or discriminant score. See FIG. 2A. From Terminal E (FIG. 2F), the method 2000 proceeds to block 2050 where the method 2000 defaults to predetermined classifier parameters, if used, that lead to a low false negative diagnosis unless a user of the medical device 100 specifies a desired level of sensitivity/specificity. The low false negative diagnosis allows the nodule screener 106 of the medical device 100 to minimize the number of malignant nodules that are misclassified as Type I, leading to observation not needing invasive procedures. See blocks 2052, 2056. At block 2054, for nodules that are classified as Type II by the nodule screener 106 may require invasive procedures, such as fine needle aspiration, unless they can be subclassified for further observation before execution of invasive procedures.

Various embodiments of the present subject matter allow the nodule screener to detect small malignant nodules, such as those smaller than 10 mm, if their nodule stiffness index exceeds the classifier parameters. Choosing which nodule to biopsy for patients with multiple nodules is also a challenge in managing nodules. Various embodiments of the present subject matter help to select nodules that are likely malignant for a biopsy while bypassing nodules that are likely to be benign. Aggressive biopsy of nodules is costly. Various embodiments of the present subject matter facilitate the medical device 100 and may help so to better utilize healthcare resources in managing nodules.

Thyroid nodules are considered an epidemic due to the large number of imaging studies performed and the increasing incidental detection (annual incidence rate of 0.1%) of these nodules. Since the existing imaging modalities (CT, MRI and ultrasound) cannot accurately differentiate between the malignant and benign nodules with a high level of confidence, an FNA biopsy, which costs more than $1,200 including an ultrasound exam in an institution, is performed on nodules showing suspicious features. However, the majority of FNA procedures are performed on benign nodules, e.g., 76.9% in our study population. Thus, by screening many benign nodules from an FNA procedure altogether, costs associated with FNA biopsies for patients with benign nodules may be reduced. In addition, although FNA is a minimally invasive procedure, it can take a toll on patients emotionally, especially in patients who are fearful of procedures requiring the use of needles. Thus, a noninvasive pre-FNA triage tool to screen out benign nodules with a high level of confidence can be of significant benefit to patients and health care expenditures.

By dividing Type-II nodules into two subgroups by the nodule screener 106, it may be possible to have a short-term ultrasound follow-up exam for patients with a Type IIa nodule without any suspicious ultrasound features or family history of thyroid cancer, which would further reduce the number of biopsies performed by screening both Type-I and Type-IIa nodules. On the other hand, if a patient with a Type IIa nodule had a previous history of cancer or if the nodule shows suspicious features, then the patient may be referred for an FNA biopsy. In a case where the patient has a Type IIb nodule, immediate FNA or surgery is likely to be recommended. FNA biopsy is considered a standard procedure for managing nodules and has been shown to be accurate for diagnosing nodules when used in conjunction with ultrasound. Various embodiments of the present invention use elastography to supplement FNA biopsies by screening out nodules that are highly likely to be benign, thereby decreasing the number of FNA biopsies performed. Returning to FIG. 2F, the method 200 continues to exit Terminal F and terminates execution.

While illustrative embodiments have been illustrated and described, it will be appreciated that various changes can be made therein without departing from the spirit and scope of the invention.

The embodiments of the invention in which an exclusive property or privilege is claimed are defined as follows:

1. A medical device for diagnosing malignant nodules in a bodily organ, comprising:
   an ultrasound elastographer configured to quantify tissue strain generated by either in vivo compression or external compression of the bodily organ to produce elastography information;
   a benign/malignant scorer configured to transform elastography information of each nodule into a nodule stiffness index, at least in part, by:
   a) using systolic information by taking a ratio of a highest strain near an in vivo compression source and a lowest strain in the nodule; or
   b) using diastolic information by calculating a standard deviation of strain variation in diastole of an in vivo compression source; or
   c) calculating a discriminant score based on frequency characteristics of a strain rate waveform for a nodule; and
   a nodule screener configured to classify a nodule as Type I, which is benign for further observation, or as Type II, which is malignant for invasive procedures, wherein the nodule screener is configured to classify the nodule based, at least in part, on the nodule stiffness index.

2. A method for diagnosing benign nodules in a bodily organ, comprising:
   performing an elastography process to derive quantitative information on tissue stiffness so as to produce a set of strain frames;
   calculating for each nodule a nodule stiffness index using the set of strain frames, wherein said calculating comprises:
   using systolic information by taking a ratio of a highest strain near an in vivo compression source and a lowest strain in the nodule; or
   using diastolic information by calculating a standard deviation of strain variation in diastole of an in vivo compression source; or
   calculating a discriminant score based on frequency characteristics of a strain rate waveform for a nodule; and
   screening each nodule to classify the nodule as Type I, which is benign for further observation, or as Type II, which is malignant for invasive procedures.

3. The method of claim 2, wherein calculating the nodule stiffness index includes calculating the nodule stiffness index using systolic information by taking a ratio of a highest strain near an in vivo compression source and a lowest strain in the nodule.

4. The method of claim 2, wherein calculating the nodule stiffness index includes calculating the nodule stiffness index using diastolic information by calculating a standard deviation of strain variation in diastole of an in vivo compression source.

5. The method of claim 2, wherein calculating the nodule stiffness index includes calculating a discriminant score based on frequency characteristics of a strain rate waveform for a nodule.

6. The method of claim 5, wherein calculating the nodule stiffness index includes calculating k-means clustering strain rate waveforms that respond similarly to the in vivo compression source, calculating further including selecting a mean strain rate waveform with the lowest amplitude.

7. The method of claim 6, wherein calculating the nodule stiffness index yet further includes calculating a power spectrum of the mean strain rate waveform, calculating additionally including reducing feature dimensionality by converting into a space with fewer dimensions.

8. The method of claim 7, wherein calculating the nodule stiffness index includes performing linear discriminant analysis over the space with fewer dimensions to produce the discriminant score.

9. A non-transitory computer-readable medium having computer-executable instructions stored thereon for implementing a method for diagnosing benign nodules in a bodily organ, comprising:
   performing an elastography process to derive quantitative information on tissue stiffness so as to produce a set of strain frames;
   calculating for each nodule a nodule stiffness index using the set of strain frames, wherein said calculating comprises:
   using systolic information by taking a ratio of a highest strain near an in vivo compression source and a lowest strain in the nodule; or
   using diastolic information by calculating a standard deviation of strain variation in diastole of an in vivo compression source; or
   calculating a discriminant score based on frequency characteristics of a strain rate waveform for a nodule; and
   screening each nodule to classify the nodule as Type I, which is benign for further observation, or as Type II, which is malignant for invasive procedures.

10. The computer-readable medium of claim 9, wherein calculating the nodule stiffness index includes calculating the nodule stiffness index using systolic information by taking a ratio of a highest strain near an in vivo compression source and a lowest strain in the nodule.

11. The computer-readable medium of claim 9, wherein calculating the nodule stiffness index includes calculating the nodule stiffness index using diastolic information by calculating a standard deviation of strain variation in diastole of an in vivo compression source.

12. The computer-readable medium of claim 9, wherein calculating the nodule stiffness index includes calculating a discriminant score based on frequency characteristics of a strain rate waveform for a nodule.

13. The computer-readable medium of claim 12, wherein calculating includes k-means clustering strain rate waveforms that respond similarly to the in vivo compression source, calculating the nodule stiffness index further including selecting a mean strain rate waveform with the lowest amplitude.

14. The computer-readable medium of claim 13, wherein calculating the nodule stiffness index yet further includes calculating a power spectrum of the mean strain rate waveform, calculating additionally including reducing feature dimensionality by converting into a space with fewer dimensions.

15. The computer-readable medium of claim 14, wherein calculating the nodule stiffness index includes performing linear discriminant analysis over the space with fewer dimensions to produce the discriminant score.

\* \* \* \* \*